United States Patent
Jeong (10) Patent No.: US 11,443,844 B2
(45) Date of Patent: Sep. 13, 2022

(54) SMART TRAY FOR MEASURING FOOD INTAKE AND WEIGHT CHANGE, AND WEIGHT MANAGEMENT SYSTEM COMPRISING SAME

(71) Applicant: Kwang-Cheol Jeong, Goyang-si (KR)

(72) Inventor: Kwang-Cheol Jeong, Goyang-si (KR)

( * ) Notice: Subject to any disclaimer, the term of this patent is extended or adjusted under 35 U.S.C. 154(b) by 795 days.

(21) Appl. No.: 16/319,146

(22) PCT Filed: Jul. 18, 2017

(86) PCT No.: PCT/KR2017/007720
§ 371 (c)(1),
(2) Date: Jan. 18, 2019

(87) PCT Pub. No.: WO2018/016846
PCT Pub. Date: Jan. 25, 2018

(65) Prior Publication Data
US 2021/0335475 A1    Oct. 28, 2021

(30) Foreign Application Priority Data

Jul. 20, 2016  (KR) .......................... 10-2016-0091748

(51) Int. Cl.
*G16H 20/60* (2018.01)
*G01G 19/414* (2006.01)
*G01G 19/44* (2006.01)
*G08B 21/18* (2006.01)
*H04N 5/225* (2006.01)
(Continued)

(52) U.S. Cl.
CPC ......... *G16H 20/60* (2018.01); *G01G 19/4146* (2013.01); *G01G 19/44* (2013.01); *G08B 21/182* (2013.01); *H04N 5/2257* (2013.01); *H04N 5/232* (2013.01); *H04Q 9/00* (2013.01); *H04Q 2209/40* (2013.01)

(58) Field of Classification Search
CPC .... G16H 20/60; G01G 19/4146; G01G 19/44; G08B 21/182; H04N 5/2257; H04N 5/232; H04Q 9/00; H04Q 2209/40
See application file for complete search history.

(56) References Cited

U.S. PATENT DOCUMENTS

2014/0349257 A1* 11/2014 Connor .................. G16H 20/60
434/127
2016/0173830 A1*  6/2016 Watanabe .......... H04N 5/23206
348/143
2016/0321951 A1* 11/2016 Kim ....................... G06Q 99/00

FOREIGN PATENT DOCUMENTS

| JP | 2015-225460 A |   | 12/2015 |
| JP | 2015225460 A | * | 12/2015 |
| KR | 10-2006-0007236 A |   | 1/2006 |

(Continued)

*Primary Examiner* — Amine Benlagsir
(74) *Attorney, Agent, or Firm* — Maschoff Brennan (57) ABSTRACT

The present invention relates to a smart tray for measuring a food intake and a weight change, and a weight management system comprising the smart tray, the smart tray comprising: a weight sensor for detecting the weight of an object placed on the upper surface and generating object weight information; an input unit for inputting the current weight information of an eater; and a control unit for controlling the weight sensor, generating weight deduction information, which is a value deducted from the object weight information, as food intake information within a predetermined time, and, by using same, generating estimated changed weight information.

11 Claims, 4 Drawing Sheets

(51) Int. Cl.
*H04N 5/232* (2006.01)
*H04Q 9/00* (2006.01)

(56) References Cited

FOREIGN PATENT DOCUMENTS

| | | | | |
|---|---|---|---|---|
| KR | 20060007236 A | * | 1/2006 | |
| KR | 10-2009-0105897 A | | 10/2009 | |
| KR | 20090105897 A | * | 10/2009 | |
| KR | 10-2013-0117613 A | | 10/2013 | |
| KR | 20130117613 A | * | 10/2013 | |
| KR | 10-2016-0017483 A | | 2/2016 | |

* cited by examiner

SMART TRAY FOR MEASURING FOOD INTAKE AND WEIGHT CHANGE, AND WEIGHT MANAGEMENT SYSTEM COMPRISING SAME

TECHNICAL FIELD

The present invention relates to a smart tray for measuring food intake and a change in body weight, as well as a weight management system including the same.

BACKGROUND ART

In recent years, food culture has been westernized leading to an increase in the number of overweight and obese patients and, as a countermeasure for treatment and prevention of such problems, importance of exercise programs and food ingestion control is emphasized. In response to such interest, diet specialized restaurants have appeared to help diet and food ingestion control.

In particular, with regard to weight loss, food ingestion control is further emphasized, and therefore, a lot of ideas for helping diet and food ingestion regulation have been developed. One of such idea was to develop a container for measuring food intake in real time. However, in order to control such food intake by the conventional art, a cumbersome process of placing individual foods in separate bowls and then measuring and recording weight of each food, followed by measuring the food remaining after finishing the meal should be implemented. Therefore, weighing the food intake is substantially not executed.

Moreover, using the above container to regulate food ingestion involves many discomforts. In fact, in order to know the food intake, it is necessary to measure only a pure mass of the food to be ingested. However, in a typical meal course, a change in weight of food may be detected for a variety of reasons. For instance, if a bowl or cutlery is moved or removed during the meal, the weight of the bowl or cutlery is duly excluded from food intake. However, there was no consideration for the above condition in the conventional art.

Further, the fact that some food materials to be discarded without intake such as bones or shells contained in the food should not be included in food intake has not been considered.

In addition, there is a need to encourage a person who wants to go on a diet by immediately informing the person having a meal how much their body weight is altered depending on food intake even during the meal.

DISCLOSURE

Technical Problem

An object of the present invention is to provide a smart tray that measures food intake and a change in body weight and gives information on the same in real-time to a person who wants to lose weight, thereby inspiring diet desire and maximizing diet effects, as well as a body weight management system including the same.

Technical Solution

According to one embodiment of the present invention in order to achieve the above object, a smart tray for measuring food intake and a change in body weight may include: a weight sensor to sense a weight of each item placed on the top surface of the sensor and generate weight information of the item ('item weight information'); an input unit to input current body weight information of a person who consumes food ('eater'); and a control unit that controls the weight sensor to generate weight deduction information, which is a value subtracted from the item weight information in a predetermined time, as food intake information and generates estimated body weight information, which was changed, using the food intake information.

In this regard, the smart tray for measuring food intake and a change in body weight may further include a display unit, wherein the control unit may display the food intake information, the current body weight information and the estimated body weight information on the display unit.

In this regard, the smart tray for measuring food intake and a change in body weight may further include a communication unit to communicate with an external smartphone, wherein the control unit may transmit the food intake information, the current body weight information and the estimated body weight information to the external smartphone through the communication unit.

The communication unit may receive the current body weight information from an external body weight scale.

The control unit may analyze the weight deduction information and can determine that, if the weight deduction information is equal to or greater than a predetermined value within the predetermined time, this is not the food intake information.

In this regard, the smart tray for measuring food intake and a change in body weight may further include a camera unit for generating image information of the eater ('eater image information') regarding characteristics of the eater, wherein the control unit may analyze the eater image information and can determine whether or not to add the weight deduction information to the current body weight information.

In this regard, the control unit may control a camera to become pop-up when the item weight information is received by the weight sensor.

In this regard, the smart tray for measuring food intake and a change in body weight may further include an alarm unit, wherein the control unit may compare target body weight information input by the input unit with the estimated body weight information and, if the estimated body weight information is higher than the target body weight information, may operate the alarm unit.

In this regard, the smart tray for measuring food intake and a change in body weight may further include a timer, wherein the estimated body weight information may include ingestion time information acquired by the timer as well as the current body weight information and the food intake information.

In this regard, the smart tray for measuring food intake and a change in body weight may further include a communication unit to communicate with an external smartphone and an external body weight scale, wherein the control unit may acquire actually altered body weight information, which is body weight information after a meal, from the external body weight scale and compare the actually altered body weight information with the estimated body weight information, so as to generate correction information.

In this regard, the smart tray for measuring food intake and a change in body weight may further include a memory, wherein the control unit may accumulate the current body weight information, the food intake information and the actually altered body weight information in a predetermined period of time, generate a food intake-body weight change database and then store the same in the memory.

In this regard, the control unit may generate estimated body weight change information using the food intake-body weight change database.

In this regard, the food intake information may be deleted or input through the input unit.

According to another embodiment of the present invention, a body weight management system may include: a body weight scale to generate current body weight information of an eater; a smart tray, wherein the smart tray includes a weight sensor to sense a weight of each item placed on the top surface of the sensor and generate item weight information, a communication unit to communicate with a mobile communication terminal and the body weight scale, and a control unit that receives the current body weight information through the communication unit, controls the weight sensor to generate weight deduction information, which is a value subtracted from the item weight information in a predetermined time, as food intake information, and generates estimated body weight information, which was changed, using the food intake information; and the mobile communication terminal to receive the food intake information, the current body weight information and the estimated body weight information from the smart tray.

Advantageous Effects

According to one embodiment of the present invention, with the above configurations, a user can check a change in body weight based on a size of the user's meal and thus may effectively suppress an amount of food to eat.

Further, according to one embodiment of the present invention, the user can avoid an error due to behavior other than food ingestion during a meal, thereby more accurately forecasting a change in body weight by the amount of food ingested.

BEST MODE

Hereinafter, preferred embodiments of the present invention will be described in detail with reference to the accompanying drawings. The embodiments of the present invention may be modified in various forms, and the scope of the present invention is duly not construed to be particularly limited to such embodiments as described below. These embodiments are provided for more concretely explaining the present invention in order to aid in understanding of persons who have ordinary knowledge in the art, to which the present invention pertains.

Figure 1:
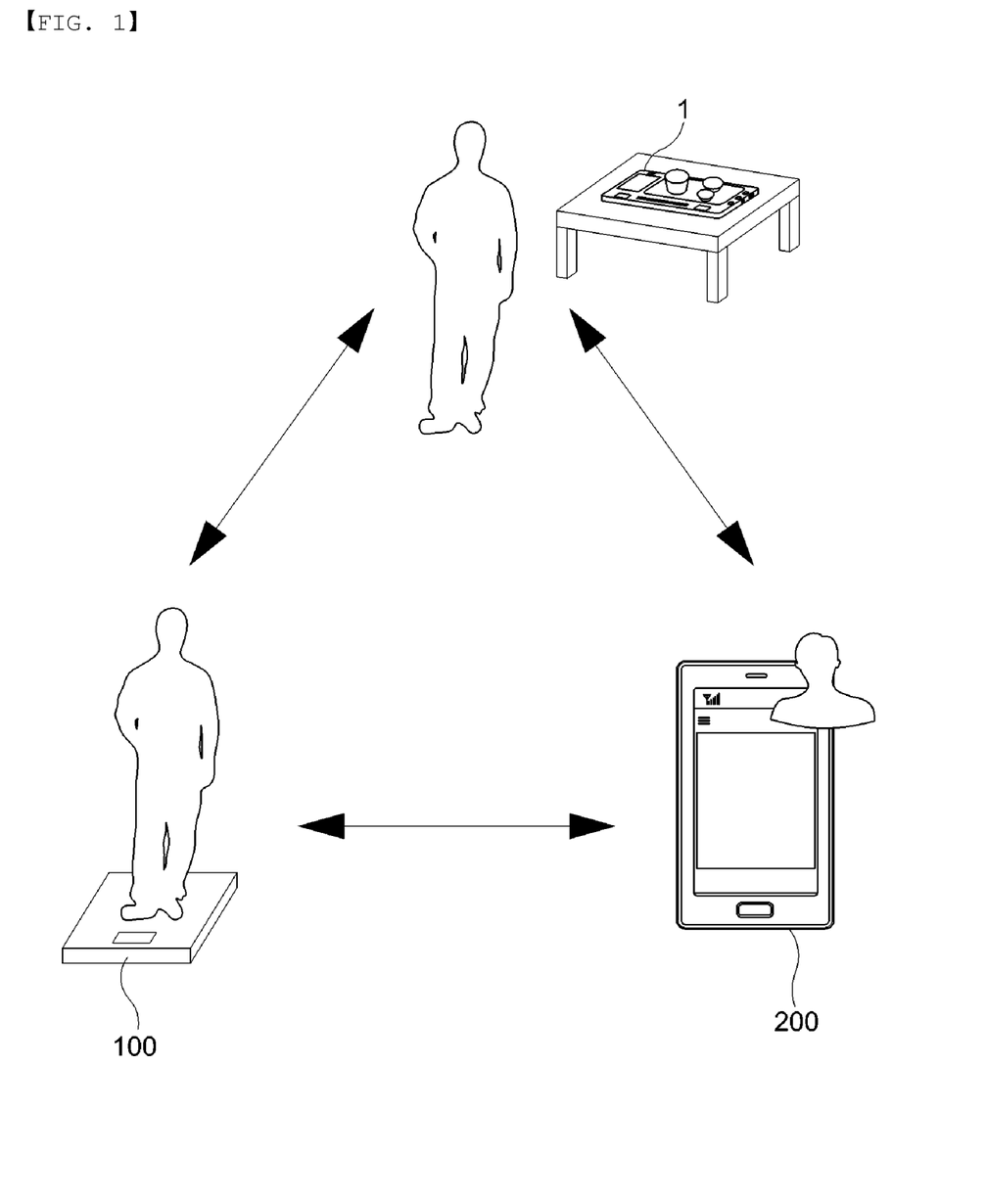
FIG. 1 is a diagram illustrating a concept of a body weight management system including the smart tray according to one embodiment of the present invention.

FIG. 1 is a diagram illustrating a concept of a body weight management system including the smart tray 1 according to one embodiment of the present invention. As shown in FIG. 1, the body weight management system according to the present invention may consist of the smart tray 1, a body weight scale 100 and a smartphone 200 ('mobile communication terminal').

The smart tray 1 may measure an amount of food actually ingested by a user (that is, an eater), check a change in body weight due to food intake and display the same, thereby functioning to inspire diet desire of the user. More particularly, the smart tray 1 may include: a weight sensor 15 to sense a weight of an item (a container filled with food) placed on the top surface of the sensor and generate item weight information; a communication unit 16 to communicate with the mobile communication terminal 200 and the body weight scale 100; and a control unit 22 that receives the current body weight information through the communication unit 16 and controls the weight sensor 15 to generate weight deduction information, which is a value subtracted from the item weight information in a predetermined time, as food intake information, and generates estimated body weight information, which was changed, using the food intake information. Hereinafter, appearance, configurations and operation of the smart tray will be described in more detail with reference to FIGS. 2 to 4.

The body weight scale 100 may function to measure actual body weight of the user, generate current body weight information of the user and transmit the same to the smart tray 1 or the mobile communication terminal 200.

The mobile communication terminal 200, that is, the smartphone may receive the food intake information and the current body weight information from the smart tray 1 to generate estimated body weight information or correction information, and therefore, can help to more accurately forecast a change in body weight.

Hereinafter, referring to FIGS. 2 to 4, the smart tray 1 according to one embodiment of the present invention will be described in more detail.

Figure 2:
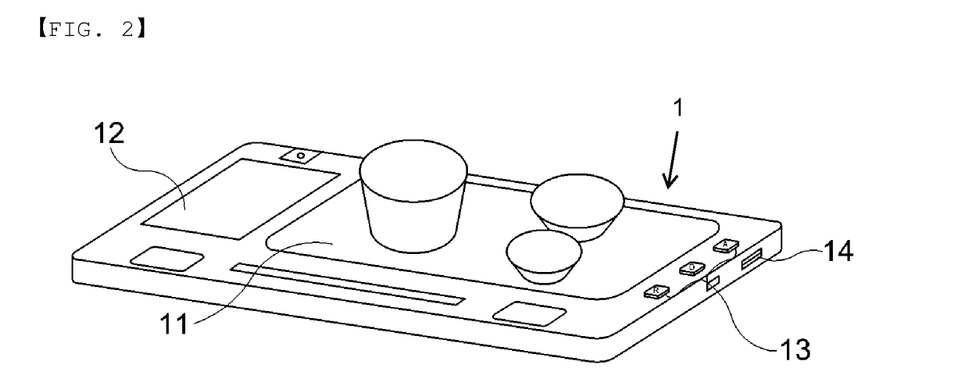
FIG. 2 is a perspective view illustrating the smart tray according to one embodiment of the present invention.

FIG. 2 is a perspective view illustrating the smart tray 1 according to one embodiment of the present invention. As shown in the drawing, the smart tray 1 may be configured in a rectangular plate form. Most of the main surface may be occupied by a container plate 11 on which a food container, an empty bowl or cutlery such as spoons and chopsticks are placed, wherein a weight sensor 15 is mounted on the bottom surface of the container plate 11 and functions to generate weight information of items (including food, cutlery, containers and bowls).

Next to the container plate 11, a display unit 12 may be provided. The display unit 12 may be a touchscreen to indicate a variety of GUI information. In the case of the touchscreen, the display unit 12 may also be operated as an input unit 13. The display unit 12 may display the current body weight information, the food intake information, the estimated body weight information (which was changed), alarm information and so on, and the user may have a meal while watching the information displayed on the display unit 12. Accordingly, the user may be further encouraged or inspired to decrease an amount of food to eat, that is, reduce the size of a meal.

Further, an input button 13 may be installed close to or at the lateral face of the container plate. Such an input button 13 is a hot key and, for example, may include a food intake check key, a food removal key or a reset key.

When pushing the food intake check key, the weight deduction information is absolutely recognized as food intake information, thereby preventing an error when the food intake information is automatically input.

Upon pushing the food removal key, the weight deduction information is never recognized as food intake information, thereby preventing an error when the food intake information is automatically input.

The reset key is a hot key for zero point adjustment, etc., wherein the user can easily proceed with user setting through the same.

On the other hand, a charge terminal 14 (or data input-output terminal) is provided at the lateral side of the container plate in order to supply electric power to the smart tray 1.

Hereinafter, with reference to FIG. 3, the electronic configuration of the smart tray 1 according to one embodiment of the present invention will be described in more detail.

Figure 3:
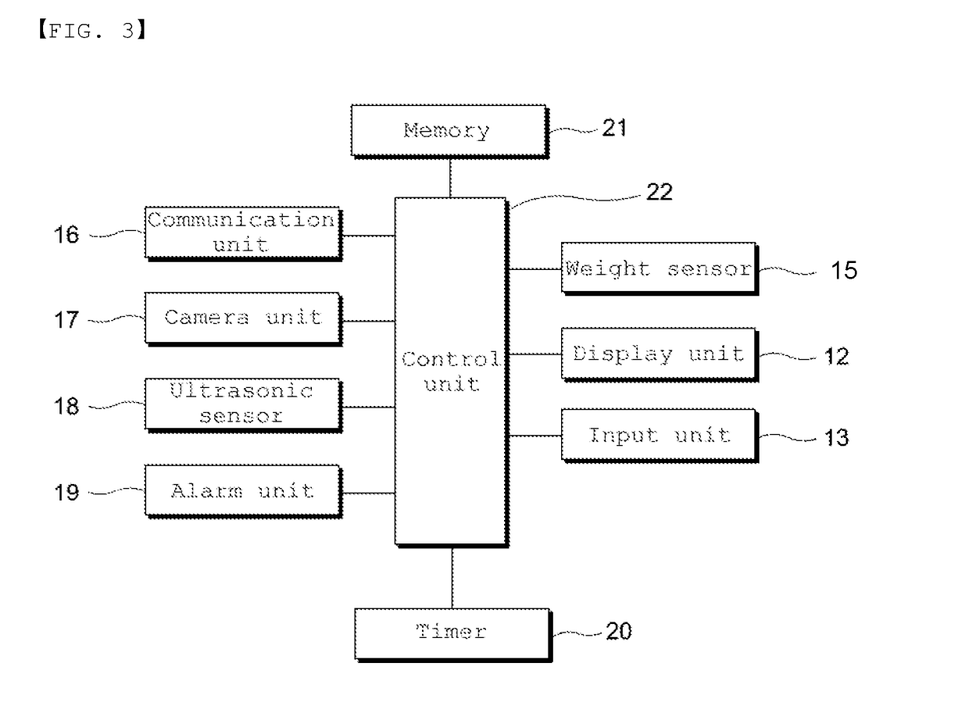
FIG. 3 is a block diagram illustrating an electronic configuration of the smart tray according to one embodiment of the present invention.

FIG. 3 is a block diagram illustrating an electronic configuration of the smart tray 1 according to one embodiment of the present invention. As shown in FIG. 3, the smart tray 1 may consist of a display unit 12, an input unit 13, a weight sensor 15, a communication unit 16, a camera unit 17, an ultrasonic sensor 18, an alarm unit 19, a timer 20, a memory 21 and a control unit 22.

The display unit 12 may be installed on a portion of the top surface of the smart tray, as shown in FIG. 2, in order to display GUI information and further indicate food intake information, estimated body weight information, current body weight information and so on.

The input unit 13 may be configured of the same components as those of the display unit 12 if the display unit 12 is a touchscreen. Alternatively, the input unit 13 may include a separate input member such as a key pad, a key button or a dial input device. The current body weight information may be input through the input unit 13, and the food intake information automatically detected may be instantly revised.

The weight sensor 15 is mounted below the container plate 11 and may function to sense a weight of an item placed on a top surface of the container plate 11. That is, the weight sensor may sense the weight of the item placed on the top surface of the container plate and then generate item weight information. In particular, the weight sensor 15 may be installed in at least three sites under the container plate 11, thereby minimizing measurement error.

The communication unit 16 is a component for data communication with an external device such as the body weight scale 100 and the mobile communication terminal 200. According to the present invention, the communication unit 16 may receive the current body weight information from the body weight scale 100 and transmit the food intake information, the current body weight information and the estimated body weight information (which is optional) to the mobile communication terminal 200, that is, the smartphone.

The camera unit 17, although not shown in FIG. 2, is a component for generating image information of the eater, which is image information of the characteristics of the eater. The camera unit may consist of a pop-up camera which is automatically being in pop-up status when a weight is sensed by the weight sensor, takes an image of the eater and generates image information of the eater. Then, the control unit 22 may analyze the eater image information so as to compensate for (or correct) the food intake information, which will be described below.

Similar to the camera unit 17, the ultrasonic sensor 18 may also generate motion information of the eater. The control unit 22 may analyze the motion information acquired by the ultrasonic sensor 18 to determine whether the eater actually eats, lifts a bowl, etc. and, based on the analyzed results, may determine whether the weight deduction information is the food intake information or not.

The alarm unit 19 may be a speaker generating alarm sound or an alarm lamp. When the food intake information exceeds the existing food intake information, the control unit 22 may operate the alarm unit to prevent the eater from continuing to eat.

The timer 20 functions to generate time information. Analysis of the food intake information, the current body weight information, the estimated body weight information and the actually altered body weight information along with the time information may predict correction information, which can more accurately forecast the estimated body weight information, and may anticipate how the actual body weight is further varied. In other words, the estimated body weight information may be generated by analyzing the current body weight information, the food intake information and the ingestion time information acquired through the timer 20

The control unit 22 functions to control overall operation of the smart tray 1 according to one embodiment of the present invention. More particularly, the control unit 22 may control the weight sensor 15 to generate weight deduction information, which is a value subtracted from the item weight information in a predetermined time, as food intake information, and may generate estimated body weight information, which was changed, using the above food intake information. Further, the control unit may display the food intake information, the current body weight information and the estimated body weight information on the display unit 12. Further, the food intake information, the current body weight information and the estimated body weight information may be transmitted through the communication unit 16 to the external smartphone 200. Further, the control unit 22 may analyze the weight deduction information and, if the weight deduction information is equal to or greater than a predetermined value in a predetermined time, may determine that the weight deduction information is not the food intake information. The control unit 22 may analyze the eater image information and determine whether or not to add the weight deduction information to the current body weight information. The control unit 22 may control the camera to become pop-up when the weight senor 15 receives the item weight information. That is, the pop-up camera is mounted on one side of the smart tray 1 and may become pop-up and start capturing images of the eater when a weight of an item is sensed on the container plate 11. Further, the control unit 22 may compare target body weight information input by the input unit with the estimated body weight information and, when the estimated body weight information exceeds the target body weight information, may operate the alarm unit 19 to lead the eater not to eat any more. Further, the control unit 22 may acquire actually altered body weight information, which is body weight information after a meal, from the external body weight scale 100, and compare this actually altered body weight information with the estimated body weight information to generate correction information. Further, the control unit 22 may accumulate the current body weight information, the food intake information and the actually altered body weight information in a predetermined period of time to generate a food intake-body weight change database and store the same in the memory 21, thereby more accurately forecasting a change in body weight to be estimated. Briefly, the control unit 22 may generate estimated body weight change information using the above food intake-body weight change database.

Hereinafter, the operation of the smart tray 1 having the above configurations will be described in more detail, with reference to the flowchart in FIG. 4.

Figure 4:
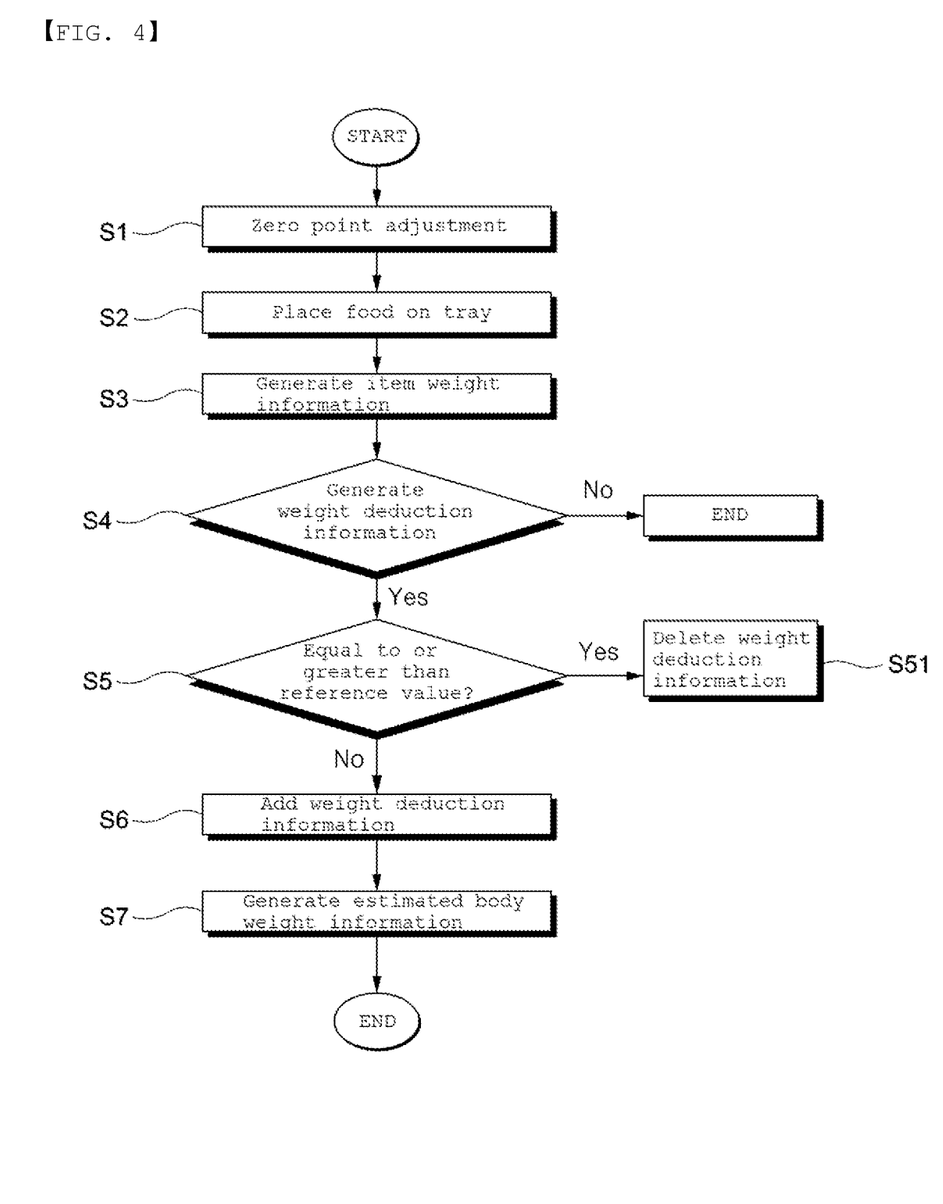
FIG. 4 is a flowchart showing exemplary operation of the smart tray of the present invention.

FIG. 4 is a flowchart showing operation of the smart tray 1 according to one embodiment of the present invention. The illustration of FIG. 4 serves to explain an example wherein the smart tray 1 is operated without data communication with any external device.

As shown in FIG. 4, first of all, zero point of the smart tray 1 is adjusted (S1). In this state, a bowl (container) including food is placed on the container plate 11 (S2). Then, the weight sensor 15 generates weight information indicating the weight of items including food, bowls, cutlery, etc. (S3). Next, a user may consume the food using the cutlery. This causes the weight sensor 15 to generate weight deduction information, which is a value subtracted from the existing item weight information by an amount of eaten food (S4). After generating the weight deduction information, analysis is executed upon the same (S5). As shown in the drawing, a first method includes checking whether the weight deduction information is equal to or greater than a reference value and, if greater than the reference value, determining that this information is not related to a meal and deleting the weight deduction information such as removing the bowls (S51). If the weight deduction information is less than the reference value, the control unit 22 recognizes and adds the weight deduction information as the food intake information (S6). Alternatively, a second method includes acquiring motion information of the eater using an ultrasonic sensor or a camera unit 17 and then analyzing the same to determine whether the weight deduction information is the food intake information or not. According to a result of the determination, the weight deduction information may be added as the food intake information. Next, the control unit 22 adds the weight deduction information to current body weight information, which was already input, so as to generate estimated body weight information and displays the same on a display unit 12 (S7). Based on the law of conservation of mass, the entirety of food intake may be turned into the body weight of the eater. Accordingly, the current body weight is immediately changed with an increase in size of the meal and such change can be instantly and visually confirmed. As such, since the estimated body weight information along the amount of food is displayed during a meal, it is possible to suppress food ingestion by the user to thus aid in dieting.

On the other hand, the food intake information as a cumulative sum of the weight deduction information is compared with preset information on an amount of food ingested at one feed and, if the food intake information exceeds the preset ingestion amount, an alarm unit 19 may be operated to prevent the eater from continuing to eat.

Hereinafter, the operation of a body weight management system including the aforementioned smart tray 1 will be described in detail, with reference to FIG. 5.

Figure 5:
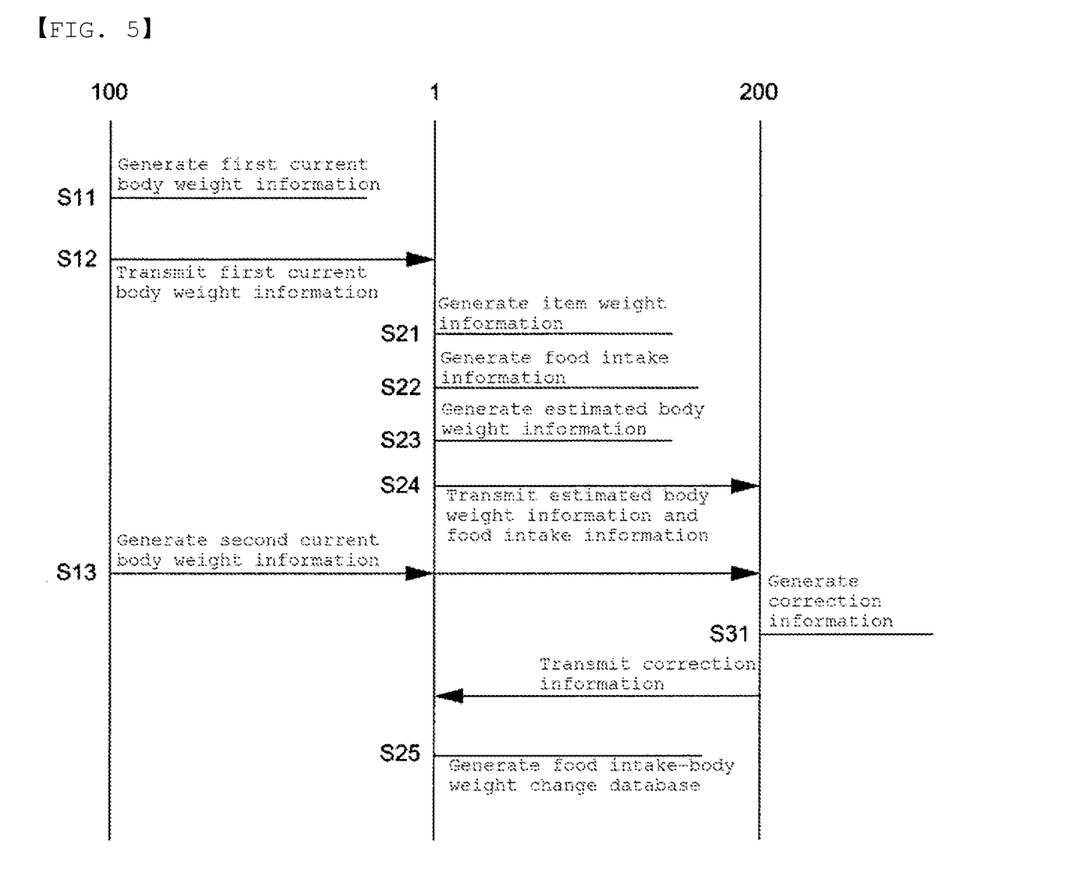
FIG. 5 is a flowchart showing operation of a body weight management system including the smart tray according to one embodiment of the present invention.

FIG. 5 is a flowchart showing operation of the body weight management system including the smart tray 1 according to one embodiment of the present invention. As shown in FIG. 5, first of all, a body weight scale 100 measures the current body weight of a user and generates current body weight information (S11). Then, this information is transmitted through a communication unit 16 to the smart tray 1 (S12). This process is a more precise way that can replace the entry of the current body weight information through an input unit as shown in FIG. 4. On the other hand, as illustrated in FIG. 4, the smart tray 1 undergoes zero point adjustment and then generates weight information of items placed on the container plate 11 (food, bowls, cutlery, etc.), that is, item weight information (S21). Further, as illustrated in FIG. 4, food intake information is generated (S22). By adding the food intake information to the current weight information, estimated body weight information is generated and then displayed on a display unit 12. In addition, the smart tray 1 transmits the estimated body weight information, the food intake information and the current body weight information (wherein user information, that is, user ID information stored in the memory 21 is included) to a mobile communication terminal 200 (S23, S24). The mobile communication terminal 200 generates correction information using the information acquired from the smart tray 1 (S31). The estimated body weight information is acquired by simply adding the food intake information to the current body weight information. However, this is not accurate body weight information since this is generally changed later due to human constitution, body weight, etc. of the user. Therefore, according to the present invention, using the user ID information, the food intake information, the current body weight information and the stored food intake-body weight change database information (wherein this information has also been stored in the smart tray 1 and the mobile communication terminal 200) may generate correction information in the mobile communication terminal 200 and transmit the same to the smart tray 1. As such, the food intake information, the current body weight information, the estimated body weight information and the correction information are added to the food intake-body weight change database (S25). Accordingly, the smart tray 1 may generate the current body weight information, the estimated body weight information (current body weight+information on an amount of ingested food) and the estimated body weight change information (information on body weight loss or body weight gain anticipated due to accumulated food intake) in accordance with the food ingestion.

According to one embodiment of the present invention having the above configurations, the user can check a change in body weight due to an amount of food ingested by the user during a meal, thereby helpfully suppressing food consumption.

Further, according to one embodiment of the present invention, the user can avoid an error caused by behavior of the user other than food ingestion during a meal, thereby more accurately forecasting a change in body weight caused by an amount of ingested food.

The aforementioned embodiments of the present invention may be configured by optionally combining all or a portion of these embodiments so as to accomplish various modifications thereof. Further, it is noted that the embodiments are for illustration but not for limitation thereof. In addition, one having ordinary knowledge in the art, to which the present invention pertains, will appreciate that a variety of embodiments are possible within the scope of the present invention.

The invention claimed is:

1. A smart tray for measuring food intake and a change in body weight, comprising:
   a weight sensor to sense a weight of each item placed on a top surface of the weight sensor and generate weight information of the each item as an item weight information;
   an input unit to input current body weight information of a person who consumes food as an eater;
   a camera unit comprising a pop-up camera which is being in pop-up status when the weight of the each item is sensed by the weight sensor, takes an image of the eater and generates image information of the eater; and a control unit that controls the weight sensor to generate weight deduction information, which is a value subtracted from the item weight information in a predetermined time, as food intake information and generates estimated body weight information, which was changed, using the food intake information, wherein the control unit analyzes the weight deduction information and, when the weight deduction information is equal to or greater than a predetermined value in the predetermined time, determines that the weight deduction information is not the food intake information, and the input unit is a key pad, a key button or a dial input device.

2. The smart tray according to claim 1, further comprising a display unit, wherein the control unit displays the food intake information, the current body weight information and the estimated body weight information on the display unit.

3. The smart tray according to claim 2, further comprising a communication unit to communicate with an external smartphone, wherein the control unit transmits the food intake information, the current body weight information and the estimated body weight information to the external smartphone through the communication unit.

4. The smart tray according to claim 3, wherein the communication unit receives the current body weight information from an external body weight scale.

5. The smart tray according to claim 1, further comprising an alarm unit, wherein the control unit compares target body weight information input through the input unit with the estimated body weight information and, when the estimated body weight information exceeds the target body weight information, operates the alarm unit.

6. The smart tray according to claim 1, further comprising a timer, wherein the estimated body weight information includes ingestion time information acquired through the timer as well as the current body weight information and the food intake information.

7. The smart tray according to claim 1, further comprising a communication unit to communicate with an external smartphone and an external body weight scale, wherein the control unit acquires actually altered body weight information, which is body weight information after a meal, from the external body weight scale, compares the actually altered body weight information with the estimated body weight information and then generates correction information.

8. The smart tray according to claim 7, further comprising a memory, wherein the control unit accumulates the current body weight information, the food intake information and the actually altered body weight information in a predetermined period of time, and then stores the current body weight information, the food intake information, and the actually altered body weight information in the memory.

9. The smart tray according to claim 8, wherein the control unit generates estimated body weight change information using a food intake-body weight change database.

10. The smart tray according to claim 1, wherein the food intake information is deleted or input through the input unit.

11. A body weight management system for measuring food intake and a change in body weight, comprising:

a body weight scale to generate current body weight information of an eater;

a smart tray, wherein the smart tray includes a weight sensor to sense a weight of each item placed on a top surface of the weight sensor and generate weight information of the each item as an item weight information, a camera unit comprising a pop-up camera which is being in pop-up status when the weight of the each item is sensed by the weight sensor, takes an image of the eater and generates image information of the eater, a communication unit to communicate with a mobile communication terminal and the body weight scale, and a control unit that receives the current body weight information through the communication unit, controls the weight sensor to generate weight deduction information, which is a value subtracted from the item weight information in a predetermined time, as food intake information, and generates estimated body weight information, which was changed, using the food intake information; and the mobile communication terminal to receive the food intake information, the current body weight information and the estimated body weight information from the smart tray, wherein the control unit analyzes the weight deduction information and, when the weight deduction information is equal to or greater than a predetermined value in the predetermined time, determines that the weight deduction information is not the food intake information, and wherein the mobile communication terminal is a smartphone.

* * * * *